(12) United States Patent
    Patil et al.

(10) Patent No.: US 10,665,133 B2
(45) Date of Patent: May 26, 2020

(54) METHOD AND SYSTEM FOR SIMULATING AN ULTRASOUND SCANNING SESSION

(71) Applicant: General Electric Company, Schenectady, NY (US)

(72) Inventors: Mahendra Madhukar Patil, Bangalore (IN); Chandan Kumar Aladahalli, Bangalore (IN); Krishna Shriram, Bangalore (IN); Rakesh Mullick, Bangalore (IN); Amit Singh, Bangalore (IN)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 398 days.

(21) Appl. No.: 15/706,039

(22) Filed: Sep. 15, 2017

(65) Prior Publication Data
    US 2018/0336803 A1    Nov. 22, 2018

(30) Foreign Application Priority Data
    May 22, 2017    (IN) .............................. 201741017923

(51) Int. Cl.
    G09B 9/00      (2006.01)
    G09B 23/28     (2006.01)
    A61B 8/00      (2006.01)
    A61B 8/08      (2006.01)

(52) U.S. Cl.
    CPC .......... *G09B 23/286* (2013.01); *A61B 8/4254* (2013.01); *A61B 8/461* (2013.01); *A61B 8/523* (2013.01); *G09B 9/00* (2013.01)

(58) Field of Classification Search
    None
    See application file for complete search history.

(56) References Cited

U.S. PATENT DOCUMENTS

| 2002/0088926 A1* | 7/2002 | Prasser ................ A61B 8/4245 250/221 |
| 2011/0170752 A1* | 7/2011 | Martin ................. G09B 23/285 382/128 |
| 2016/0328998 A1* | 11/2016 | Pedersen ................ G09B 23/28 |
| 2017/0200399 A1* | 7/2017 | Thomas ............... G09B 23/285 |

* cited by examiner

*Primary Examiner* — Bruk A Gebremichael
(74) *Attorney, Agent, or Firm* — McAndrews, Held & Malloy, Ltd.; Jacob Groethe; David Bates

(57) ABSTRACT

A system and method for simulating an ultrasound scanning session is provided. The method includes acquiring an image of at least a portion of a simulated scan surface by a camera. A probe simulator having a visually coded pattern is maneuvered on the simulated scan surface. The method includes analyzing the acquired image to identify the visually coded pattern of the probe simulator maneuvered on the simulated scan surface. The method includes determining a position and orientation of the probe simulator based on the visually coded pattern identified in the acquired image. The method includes estimating a scan plane based at least in part on the determined position and orientation of the probe simulator. The method includes retrieving an ultrasound image from storage. The ultrasound image corresponds with the estimated scan plane. The method includes presenting the retrieved ultrasound image at a display system.

20 Claims, 13 Drawing Sheets

METHOD AND SYSTEM FOR SIMULATING AN ULTRASOUND SCANNING SESSION

CROSS-REFERENCE TO RELATED APPLICATIONS/INCORPORATION BY REFERENCE

The present application claims priority to Indian Patent Application No. 201741017923, filed May 22, 2017. The content of the above-identified application is hereby incorporated herein by reference in its entirety.

FIELD

Certain embodiments of the disclosure relate to ultrasound training simulator systems and methods. More specifically, certain embodiments of the disclosure relate to a method and system for simulating an ultrasound scanning session by a simulation system having a camera tracking a visually coded pattern to determine a position and orientation of a probe simulator with respect to a simulation surface.

BACKGROUND

Essential diagnostics services such as ultrasound have long been out of reach for millions of needy people in developing countries. The unavailability of ultrasound diagnostic services has contributed to higher maternal and infant mortalities in these areas. A shortage of trained and qualified sonographers, a lack of willingness of qualified sonographers to relocate to rural areas, a poor state of infrastructure, and a high cost of ultrasound equipment are some of the factors contributing to the lack of availability of ultrasound diagnostic services in certain areas.

More recently, the availability of more affordable ultrasound devices targeting new or non-traditional users, such as midwives, paramedics, general physicians, and the like, have partially helped overcome the above-mentioned challenges. Many of these new or non-traditional users, however, have been unable to use these ultrasound devices effectively to obtain ultrasound images of a desired quality.

Conventional ultrasound classroom training methods have high costs due to the expense of the equipment, experienced instructors, infrastructure and logistics, and availability of patients for volunteer scans. In many cases, the per user cost of instructor led classroom training may be cost prohibitive in view of the compensation and incentives typically offered for newly acquired skills of the end-users. Additionally and/or alternatively, training simulators may be used to teach users to perform ultrasound scans. The sensors and other electronic circuitry typically included in a probe and scanned object (e.g., mannequin), however, may be complicated and expensive. For example, training simulators typically include several sensors, such as electromagnetic sensors, RFID readers/tags, NFC readers/tags, QR readers/codes, and/or gyroscopes, among other things, and other complex electronic circuitry in the probe and/or scanned object. A typical training simulator having sensors and other electronic circuitry in the probe and scanned object components may have a price tag around $10,000, which may be cost prohibitive for many users.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY

A system and/or method is provided for simulating an ultrasound scanning session by a simulation system, substantially as shown in and/or described in connection with at least one of the figures, as set forth more completely in the claims.

These and other advantages, aspects and novel features of the present disclosure, as well as details of an illustrated embodiment thereof, will be more fully understood from the following description and drawings.

DETAILED DESCRIPTION

Figure 1:
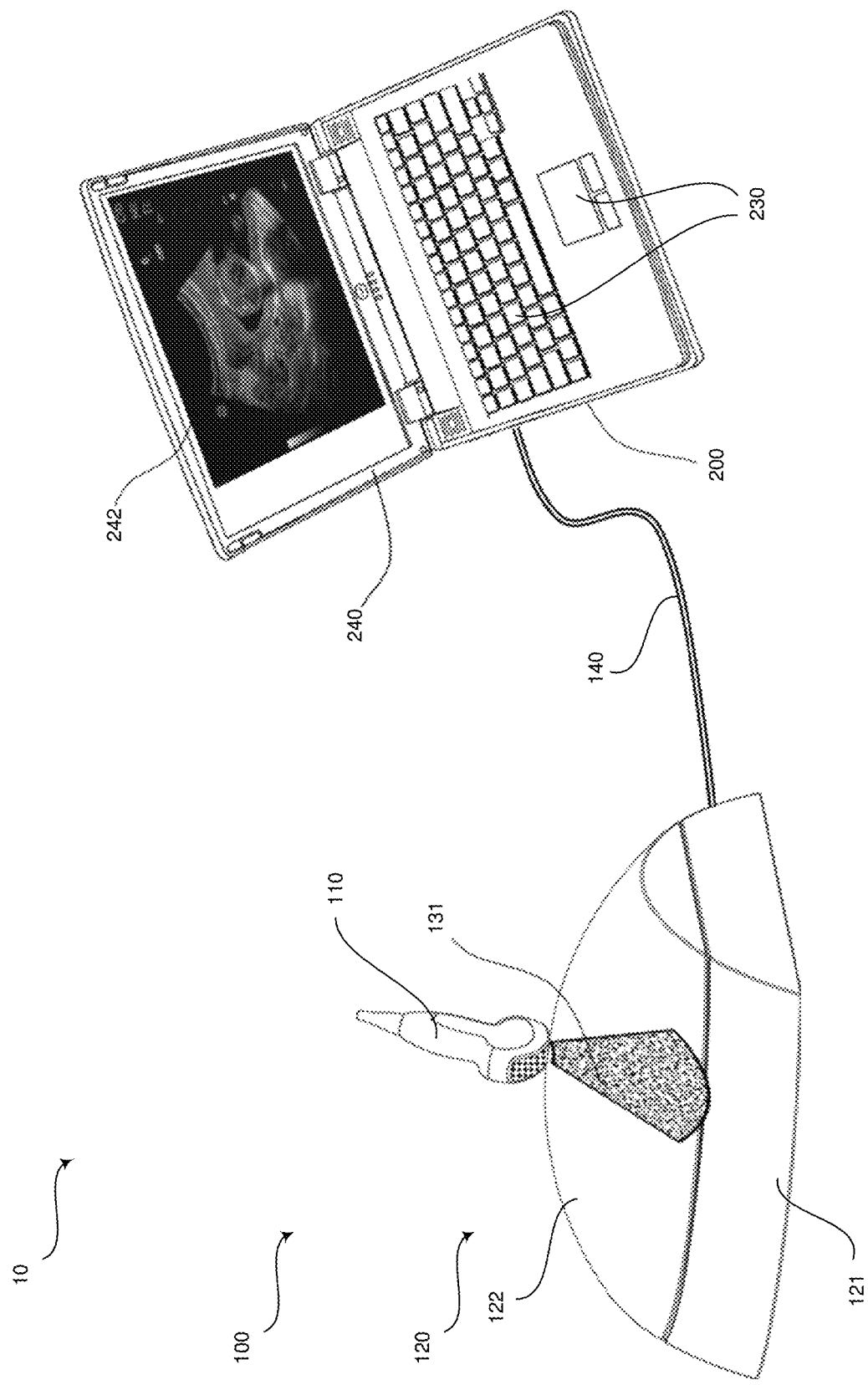
FIG. 1 illustrates an exemplary simulation system, in accordance with various embodiments.

Certain embodiments of the disclosure may be found in a method and system for simulating an ultrasound scanning session. More specifically, aspects of the present disclosure have the technical effect of providing ultrasound images corresponding with a position and orientation of a probe with respect to a simulated surface. Various embodiments have the technical effect of providing ultrasound images based on a visually coded pattern of an object that is optically tracked by a camera as either the camera or the object moves over a simulated surface.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments of the present disclosure. The following detailed description is, therefore, not to be taken in a limiting sense, and the scope of the present disclosure is defined by the appended claims and their equivalents.

As used herein, an element or step recited in the singular and proceeded with the word "a" or "an" should be understood as not excluding plural of said elements or steps, unless such exclusion is explicitly stated. Furthermore, references to "an embodiment," "one embodiment," "a representative embodiment," "an exemplary embodiment," "various embodiments," "certain embodiments," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

Furthermore, the term processor or processing unit, as used herein, refers to any type of processing unit that can carry out the calculations performed in various embodiments, such as single or multi-core: CPU, Graphics Board, DSP, FPGA, ASIC or a combination thereof.

It should be noted that various embodiments are described herein with reference to a simulation system including a probe simulator having a visually coded pattern and an anatomy simulator having a camera configured to acquire images of the visually coded pattern of the probe simulator and provide the images to a computer system for retrieving an ultrasound image corresponding with the detected position and orientation of the probe simulator. Although various examples may be provided directed to the visually coded pattern included on the probe simulator and the camera provided in the anatomy simulator, aspects of the present disclosure are not limited to this arrangement. For example, it is contemplated that the anatomy simulator may have the visually coded pattern and the probe simulator may include the camera configured to acquire images of the visually coded pattern of the anatomy simulator and provide the images to a computer system for retrieving an ultrasound image corresponding with the detected position and orientation of the probe simulator.

Figure 2:
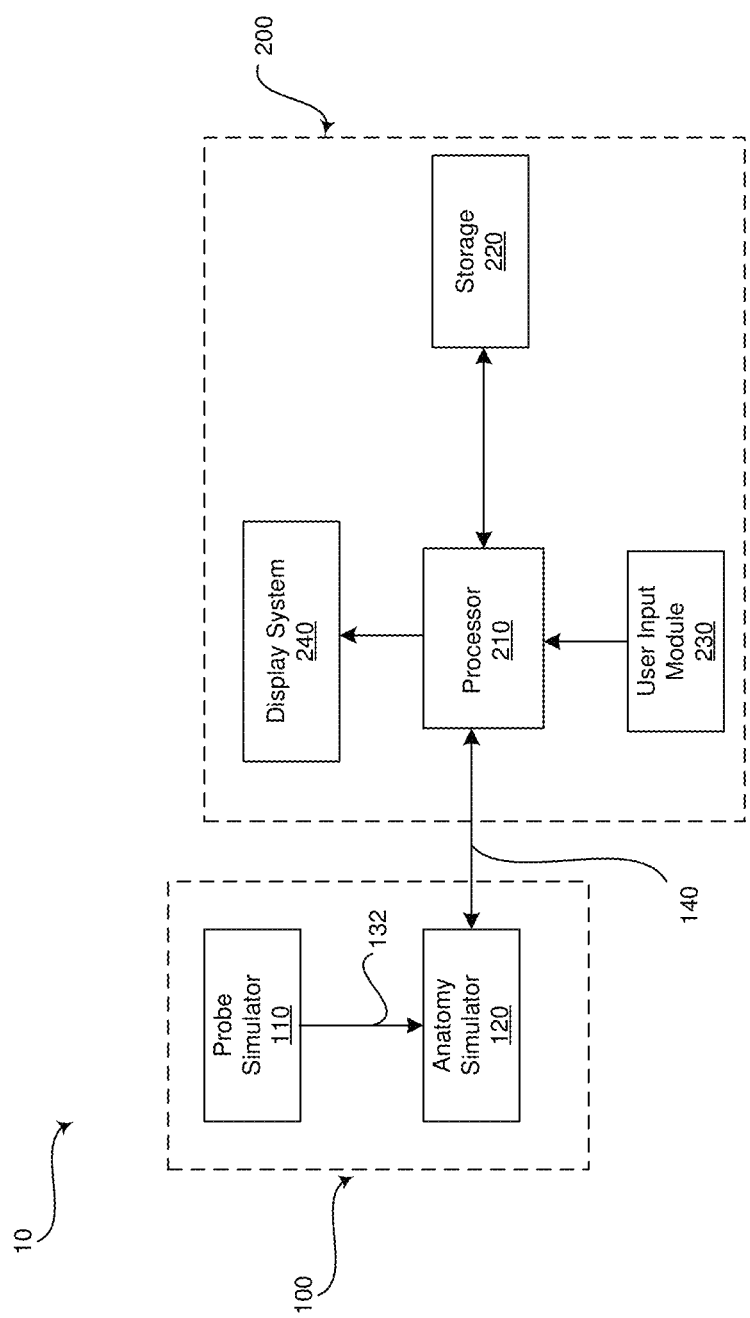
FIG. 2 is a block diagram of an exemplary simulation system, in accordance with various embodiments.

FIG. 1 illustrates an exemplary simulation system 10, in accordance with various embodiments. FIG. 2 is a block diagram of an exemplary simulation system 10, in accordance with various embodiments. Referring to FIGS. 1 and 2, the simulation system 10 includes simulators 100 and a computer system 200. The simulators 100 may include a probe simulator 110 and an anatomy simulator 120. The anatomy simulator 120 may include a base 121 and a simulated scan surface 122. The simulated scan surface 122 may be a transparent cover attached to the base 121 and shaped to generally simulate a patient's anatomy, such as a rounded surface to simulate a belly of a pregnant mother, a cavity to simulate a vaginal canal of a pregnant mother, or any suitably shaped surface. In various embodiments, the rigidity of the simulated scan surface 122 may be designed to simulate a rigidity of the patient's anatomy. The base 121 of the anatomy simulator 120 may house or be coupled to a camera 130 directed toward the transparent simulated scan surface 122 such that the camera 130 may acquire images 132 of the probe simulator 110 moving across an external surface of the simulated scan surface 122. The probe simulator 110 may include a visually coded pattern 113 that may be optically tracked by the camera 130 disposed in or on the base 121 of the anatomy simulator 120 as the probe simulator 110 is moved across the simulated scan surface 122 of the base 120. The camera 130 disposed in or on the base 121 of the anatomy simulator 120 may acquire images 132 of a portion of the simulated scan surface 122 within a field of view of the camera 130 and electronically provide the image data representative of the acquired image(s) 132 to the computer system 200 via a communication connection 140. The communications connection 140 may be a wired connection such as a Universal Serial Bus (USB) digital interface, a wireless connection such as Bluetooth providing an RF connection, or any suitable connection. In various embodiments, the anatomy simulator may be powered by an internal battery, an external battery/power supply, the computer 200 via the communications connection 140, and/or any suitable power source.

The computer system 200 may include a processor 210, storage 220, user input module 230, and a display system 240. The computer system 100 may include any number of processors 210, storage components 220, user input modules 230, and display systems 240 and is not in any way limited to the embodiment of system 200 illustrated in FIGS. 1 and 2. The components of the computer system 200 may communicate via wired and/or wireless communication, for example, and may be separate systems and/or integrated to varying degrees, for example.

The storage 220 comprises suitable logic, circuitry, interfaces and/or code that may be operable to store a simulator application, simulated ultrasound acquisition parameters, ultrasound image data, and/or any suitable information. The storage 220 may be one or more computer-readable memories, for example, such as a hard disk, floppy disk, CD, CD-ROM, DVD, compact storage, flash memory, random access memory, read-only memory, electrically erasable and programmable read-only memory and/or any suitable memory. The storage 220 may include databases, libraries, sets of information, or other storage accessed by and/or incorporated with the processor 210, for example. The storage 220 may be able to store data temporarily or permanently, for example. In various embodiments, the storage 220 stores one or more software applications, such as the simulator application. In a representative embodiment, the storage 220 may store simulated ultrasound acquisition parameters such as gain, depth, and/or any suitable parameters. In certain embodiments, the ultrasound image data may be a library of ultrasound images each associated with a probe simulator 110 position and orientation. In an exemplary embodiment, the ultrasound image data may be volumetric ultrasound image data associated with a reference coordinate system such that an ultrasound image 242 corresponding with an estimated scan plane 131 may be segmented by the processor 210 from the volumetric ultrasound image data and presented at the display system 240. In various embodiments, an array of three dimensional (3D) or four dimensional (4D) volumes may be stored and stitched together in storage 220 to cover an entire field of view of larger anatomies, such as a liver. In certain embodiments, the storage 220 may store multiple sets of ultrasound image data, such as sets of data for different anatomy types (e.g., heart, liver, fetus, etc.) and/or different anatomy positions (e.g., normal position fetus, breach position fetus, etc.). In certain embodiments, storage 220 may include cloud storage accessible over a network. The cloud storage 220 may provide access to a larger number of sets of ultrasound data and other training data. For example, a user may be provided with access to additional ultrasound data at cloud storage 220 as the user advances through a plurality of learning levels.

The user input module 230 comprises suitable logic, circuitry, interfaces and/or code that may be operable to communicate information from a user and/or at the direction of the user to the processor 210 of the system 200, for example. The user input module 230 may include button(s), a touchscreen, motion tracking, voice recognition, a mousing device, keyboard, camera, and/or any other device capable of receiving a user directive. In certain embodiments, one or more of the user input modules 230 may be integrated into other components, such as the display system 240, for example. As an example, user input module 230 may include a touchscreen display. In certain embodiments, the user input module 230 may provide instructions for selecting one of the ultrasound data sets stored in storage 220, such as an ultrasound set corresponding with a particular anatomy type (e.g., heart, liver, fetus, etc.) and/or a particular anatomy position (e.g., normal position fetus, breach position fetus, etc.). In various embodiments, the user input module 230 may provide instructions for switching between image capture (e.g., image freeze) and live display (e.g., image unfreeze) functionality. In an exemplary embodiment, the user input module 230 may provide simulated ultrasound acquisition parameters, such as gain, depth, and the like. The simulated ultrasound acquisition parameters may be used to select and/or segment the appropriate ultrasound image data and/or process ultrasound image data selected and/or segmented by the processor 210, for example.

The display system 240 comprises suitable logic, circuitry, interfaces and/or code that may be operable to communicate visual information to a user. For example, a display system 240 may include one or more monitors comprising a liquid crystal display, a light emitting diode display, and/or any suitable display. The display system 240 can be integrated with the user input module 230 to form a touchscreen display. The display system 240 may be operable to display image data selected, segmented, and/or processed by processor 210, for example.

The processor 210 comprises suitable logic, circuitry, interfaces and/or code that may be operable to execute a simulator application to control a simulation session based at least in part on image data acquired at the camera 130 of the anatomy simulator 120 of the visually coded pattern 113 of the probe simulator 110 and simulated ultrasound acquisition parameters received via the user input module 230. For example, the processor 210 may be configured to analyze the image data to determine a probe simulator 110 position and orientation based on the visually coded pattern 113 detected in the image data. In various embodiments, an estimated scan plane 131 may be determined by the processor 210 based at least in part on the probe simulator 110 position and orientation and simulated ultrasound acquisition parameters, such as a depth setting, saved in storage 220. The simulated ultrasound acquisition parameters may be default parameters or selected parameters provided via the user input module 230. In an exemplary embodiment, the processor 210 may be configured to select an ultrasound image from an image library in storage 220 corresponding with the estimated scan plane. In certain embodiments, the processor 210 may be configured to segment an image corresponding with the estimated scan plane 131 from volumetric imaging data saved in storage 220. The selected and/or segmented image may be provided by the processor 210 to the display system 240 for display. The processor 210 may be one or more central processing units, microprocessors, microcontrollers, and/or the like. The processor 210 may be an integrated component, or may be distributed across various locations, for example. The processor 210 may be capable of executing any of the method(s) 300 and/or set(s) of instructions discussed below in accordance with the present disclosure, for example.

Figure 3:
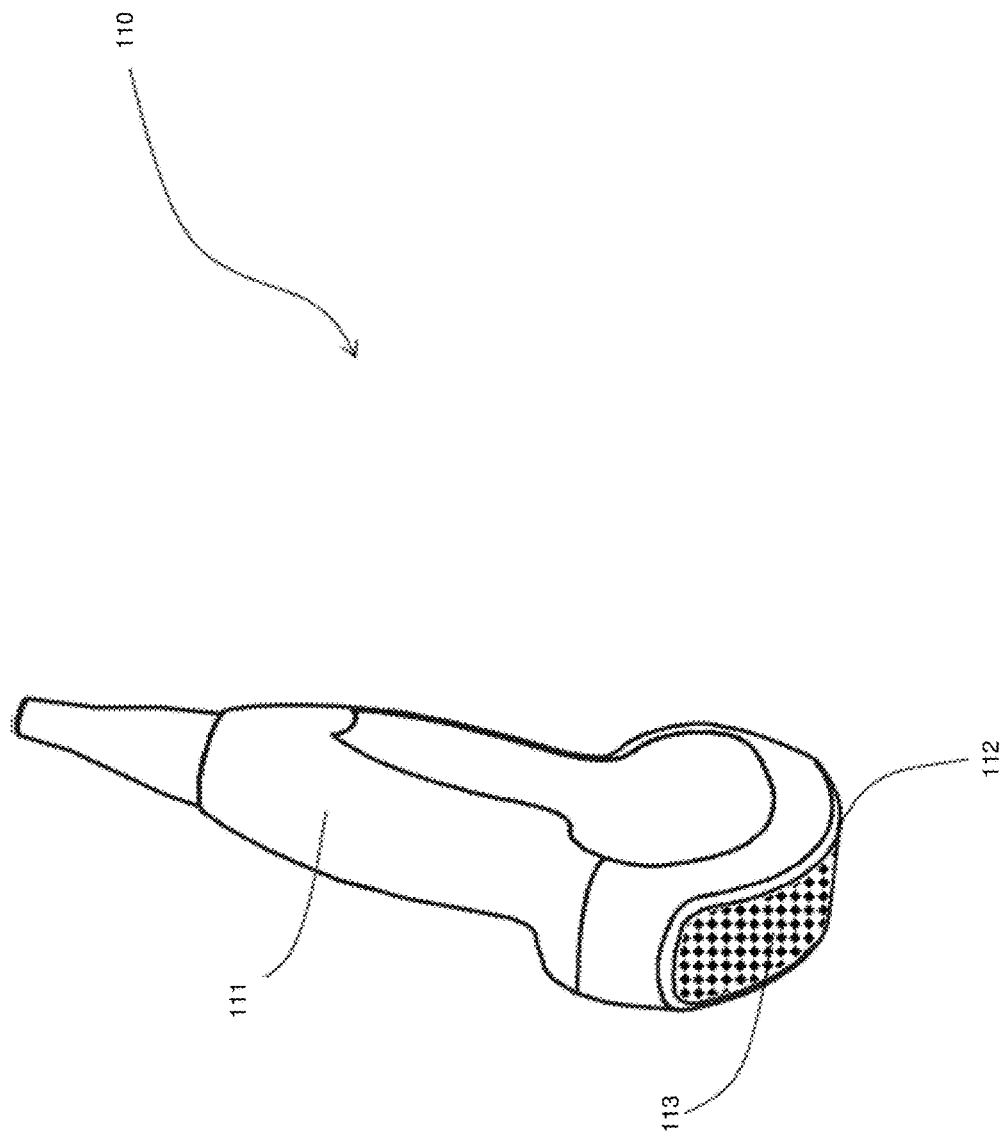
FIG. 3 is a perspective view of an exemplary probe simulator of a simulation system, in accordance with an embodiment of the disclosure.

FIG. 3 is a perspective view of an exemplary probe simulator 110 of a simulation system 10, in accordance with an embodiment of the disclosure. Referring to FIG. 3, the probe simulator 110 may include a probe body 111, a simulated transducer surface 112, and a visually coded pattern 113. The probe body 111 may be provided in a variety of shapes and sizes. For example, the probe body 111 may be sized and shaped similar to a cardiac probe, vascular probe, abdominal probe, transvaginal probe, endorectal probe, transesophageal probe, and/or any suitable probe shape and size. The simulated transducer surface 112 may be provided at an end of the probe body 111 and may include the visually coded pattern 113. The simulated transducer surface 112 may be designed to be placed against and maneuvered about a simulated scan surface 122 of an anatomy simulator 120. The visually coded pattern 113 may be a regular, irregular, or arbitrary pattern. The visually coded pattern 113 may include color coding, markers, or any suitable features designed to identify portions of the pattern 113 that can be distinguished from other portions of the pattern 113. In various embodiments, the probe body 111 may include an illumination source for providing lighting around the simulated transducer surface 112 to increase the visibility of the visually coded pattern 113 by a camera 130. In operation, the simulated transducer surface 112 may be manipulated on a simulated scan surface 122 of an anatomy simulator 120 such that a camera 130 of the anatomy simulator 120 may acquire images of the visually coded pattern 112 on the simulated transducer surface 112 that may be used by a processor 210 of a computer system 200 to determine a position and orientation of the probe simulator 110. In certain embodiments, the handheld probe simulator 110 is not connected to external devices. For example, the probe simulator 110 may be a dummy probe. Alternatively, the probe simulator 110 may include a camera configured to acquire images of a visually coded pattern in the anatomy simulator 120 and the images may be transmitted via a wired or wireless connection to the computer system 200 to determine the position and orientation of the probe simulator 110.

Figure 4:
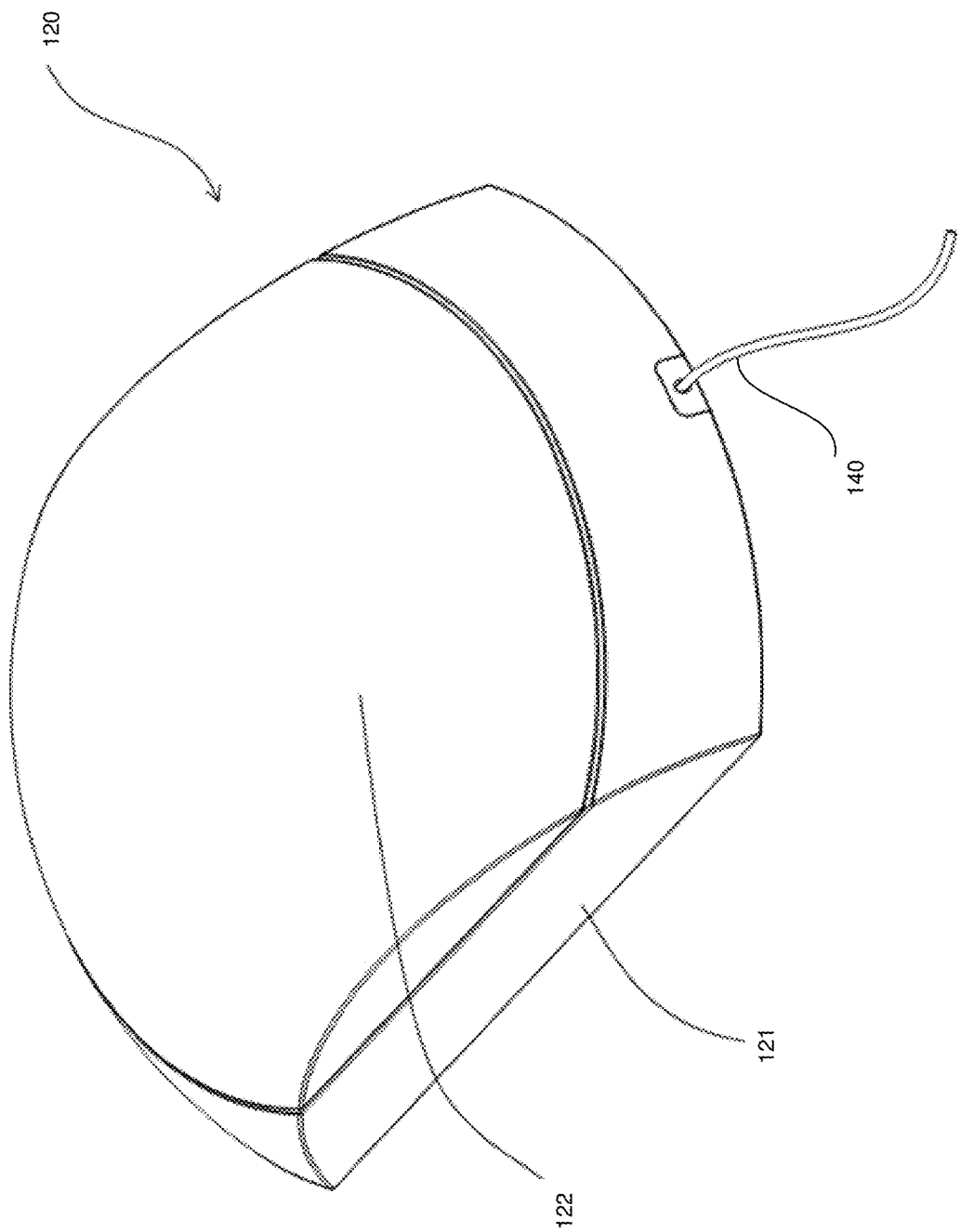
FIG. 4 is a perspective view of an exemplary anatomy simulator of a simulation system, in accordance with an embodiment of the disclosure.
Figure 5:
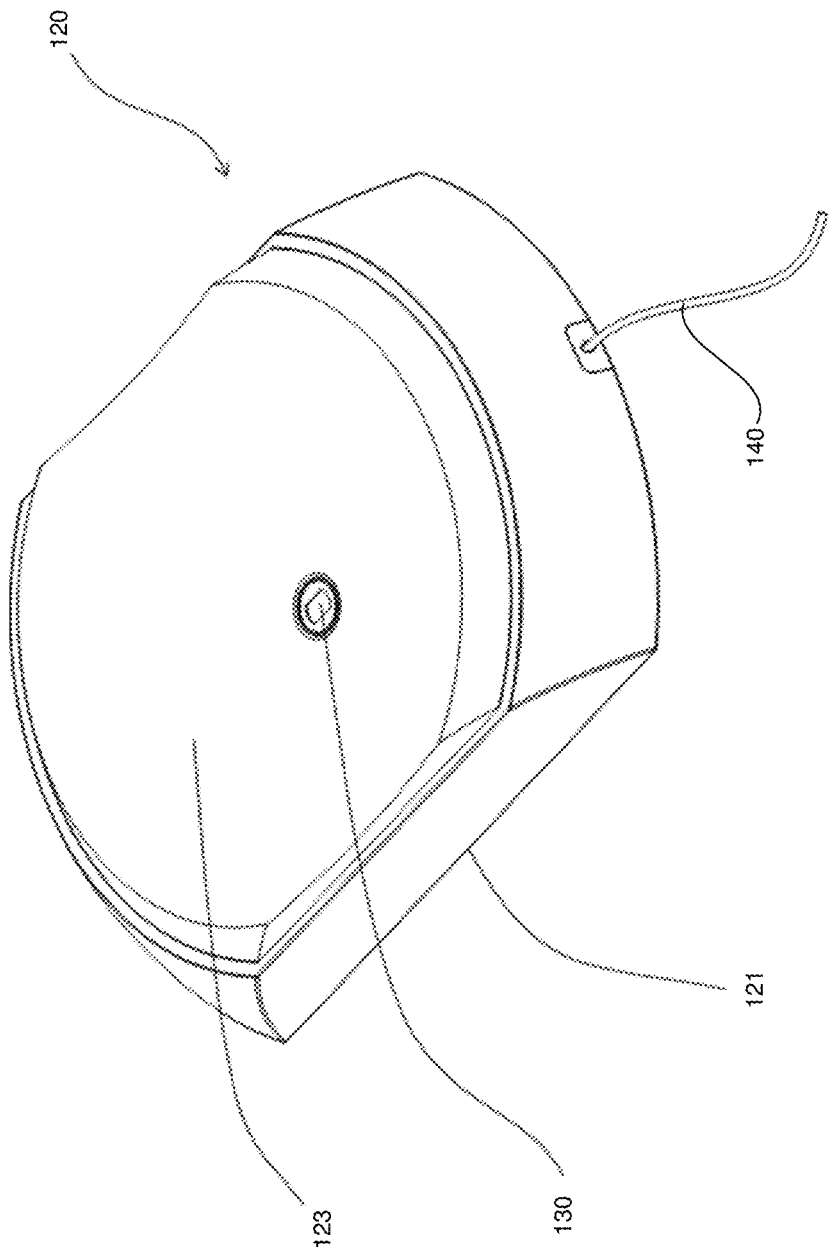
FIG. 5 is a perspective view of a base portion of an exemplary anatomy simulator of a simulation system, in accordance with an embodiment of the disclosure.

FIG. 4 is a perspective view of an exemplary anatomy simulator 120 of a simulation system 10, in accordance with an embodiment of the disclosure. FIG. 5 is a perspective view of a base portion 121 of an exemplary anatomy simulator 120 of a simulation system 10, in accordance with an embodiment of the disclosure. Referring to FIGS. 4 and 5, the anatomy simulator 120 may include a base 121 coupled to a simulated scan surface 122. The base 121 may include a top surface 123 having an opening for a camera 130 disposed within the base 121. In various embodiments, the top surface 123 may be a display screen (e.g., a light emitting diode or liquid crystal display) that may be configured to display an image 124 of a simulated internal portion of anatomy (e.g., a heart or fetus) that may be viewed by a user through the transparent simulated scan surface 122. Additionally and/or alternatively, one or more of the base 121 and the simulated scan surface 122 may include a projector configured to project an image 124 of a simulated internal portion of anatomy onto the top surface 123 of the base 121. The simulated scan surface 122 may be transparent so that a camera 130 on one side of the simulated scan surface 122 is capable of imaging a visually coded pattern 133 on an opposite side of the simulated scan surface 122. The simulated scan surface 122 may be shaped to generally simulate a patient's anatomy, such as a rounded surface to simulate a belly of a pregnant mother, a cavity to simulate a vaginal canal of a pregnant mother, or any suitably shaped surface. In certain embodiments, the rigidity of the simulated scan surface 122 may be designed to simulate a rigidity of the patient's anatomy. In various embodiments, the simulated scan surface 122 may be detachably coupled to the base 121 so that simulated scan surfaces 122 of different shape and/or rigidity may be interchangeably coupled to and used with the base 121. The camera 130 disposed in or on the base 121 of the anatomy simulator 120 may be communicatively coupled to a computer system 200 via a communications connection 140. The communications connection 140 may be a wired connection (e.g., Universal Serial Bus (USB) digital interface, etc.), a wireless connection (e.g., Bluetooth, Wi-Fi, etc.), or any suitable connection. In various embodiments, the anatomy simulator 120 may be powered by an internal battery, an external battery/power supply, the computer 200 via the communications connection 140, and/or any suitable power source.

Figure 6:
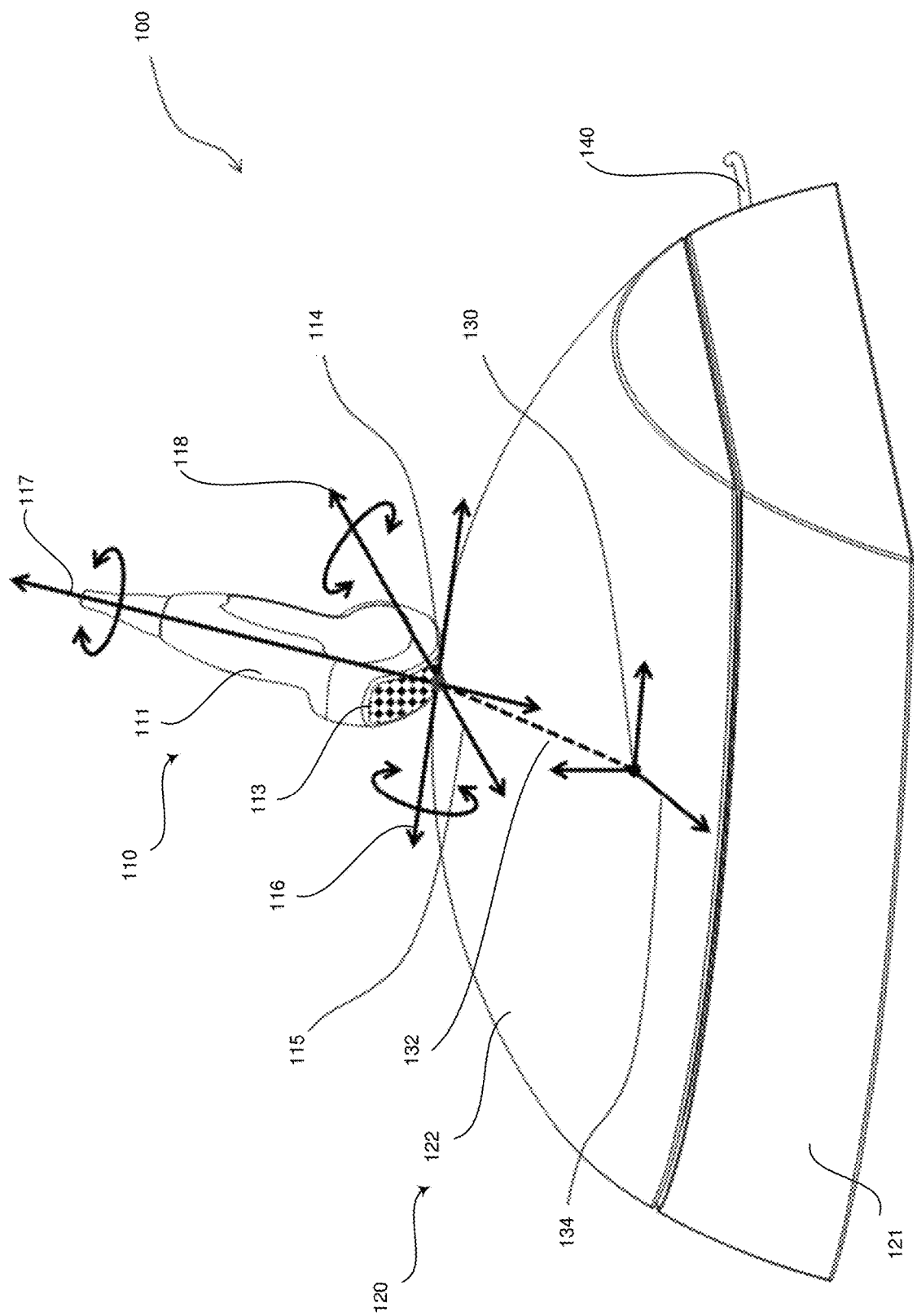
FIG. 6 is a perspective view of an exemplary probe simulator and anatomy simulator of a simulation system, in accordance with an embodiment of the disclosure.

FIG. 6 is a perspective view of an exemplary probe simulator 110 and anatomy simulator 120 of a simulation system 10, in accordance with an embodiment of the disclosure. Referring to FIG. 6, the simulation system 10 includes a probe simulator 110 and an anatomy simulator 120 communicatively coupled to a computer system 200 by a communications connection 140. The probe simulator 110 includes a probe body 111 and a visually coded pattern 113 on a simulated transducer surface 112. The anatomy simulator 120 includes a simulated scan surface 122 coupled to a base 121 having a camera 130. The probe simulator 110 may be placed on the simulated scan surface 122 at a probe placement location 114 and pivoted, turned, rotated, and/or otherwise manipulated about an X-axis 116, Y-axis 117, and/or Z-axis 118 of a probe coordinate system 115. The camera 130 may acquire image data of the visually coded pattern 113 of the probe simulator 110 at the probe placement location 114 on the simulated scan surface 122 of the anatomy simulator 120. The camera 130 may continuously acquire the image data at 30 frames/second or any suitable rate if the simulation application is operating in an unfreeze mode. The images acquired by the camera 130 and transmitted to the computer system 200 via the communications connection 140 may be associated with a reference anatomy simulator coordinate system 134. The computer system 200 may determine the position and orientation of the probe simulator 110 corresponding with the probe coordinate system 115 by analyzing the visually coded pattern 113 of the probe simulator 110 within the received image data with reference to the known anatomy simulator coordinate system 134.

The simulators 100 illustrated in FIG. 6 share various characteristics with the probe simulator 110 and anatomy simulator 120 (collectively referred to as simulators 100) illustrated in FIGS. 1-5 as described above.

Figure 7:
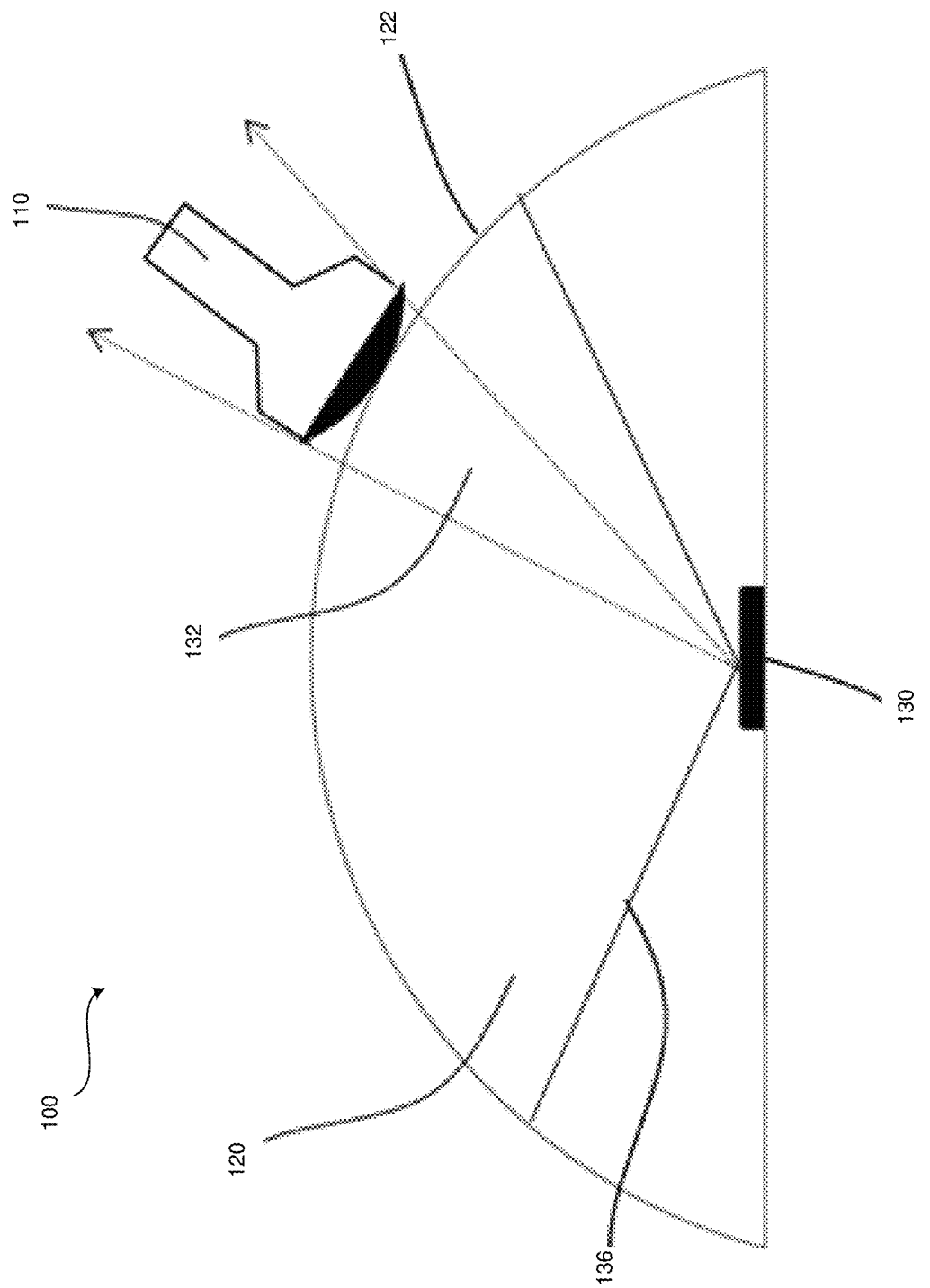
FIG. 7 illustrates an exemplary camera of an anatomy simulator acquiring image data of a probe simulator for an external simulated ultrasound examination, in accordance with an embodiment of the disclosure.
Figure 8:
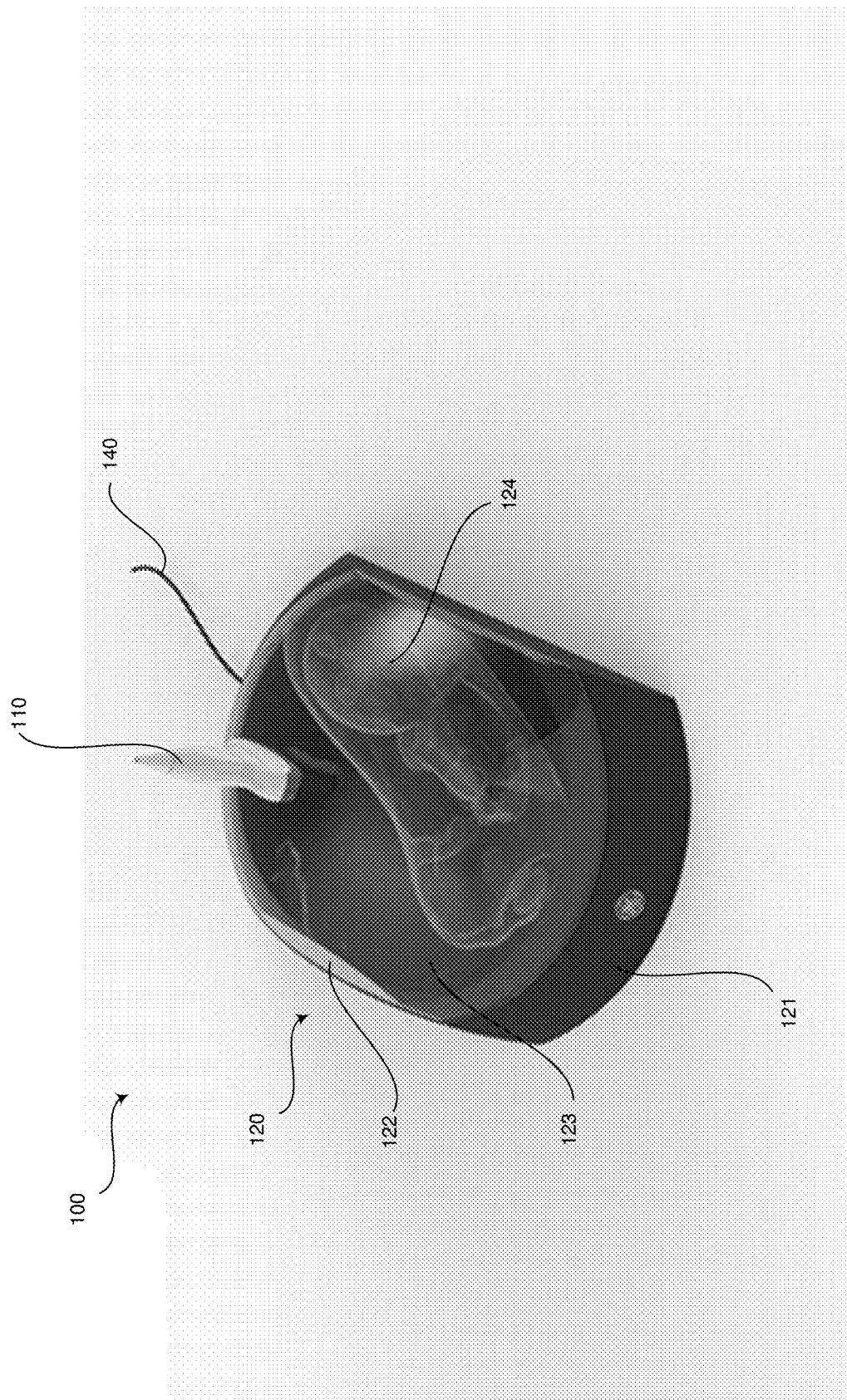
FIG. 8 is a top, perspective view of an exemplary probe simulator and anatomy simulator having a simulated scan surface configured for an external simulated ultrasound examination, in accordance with an embodiment of the disclosure.
Figure 9:
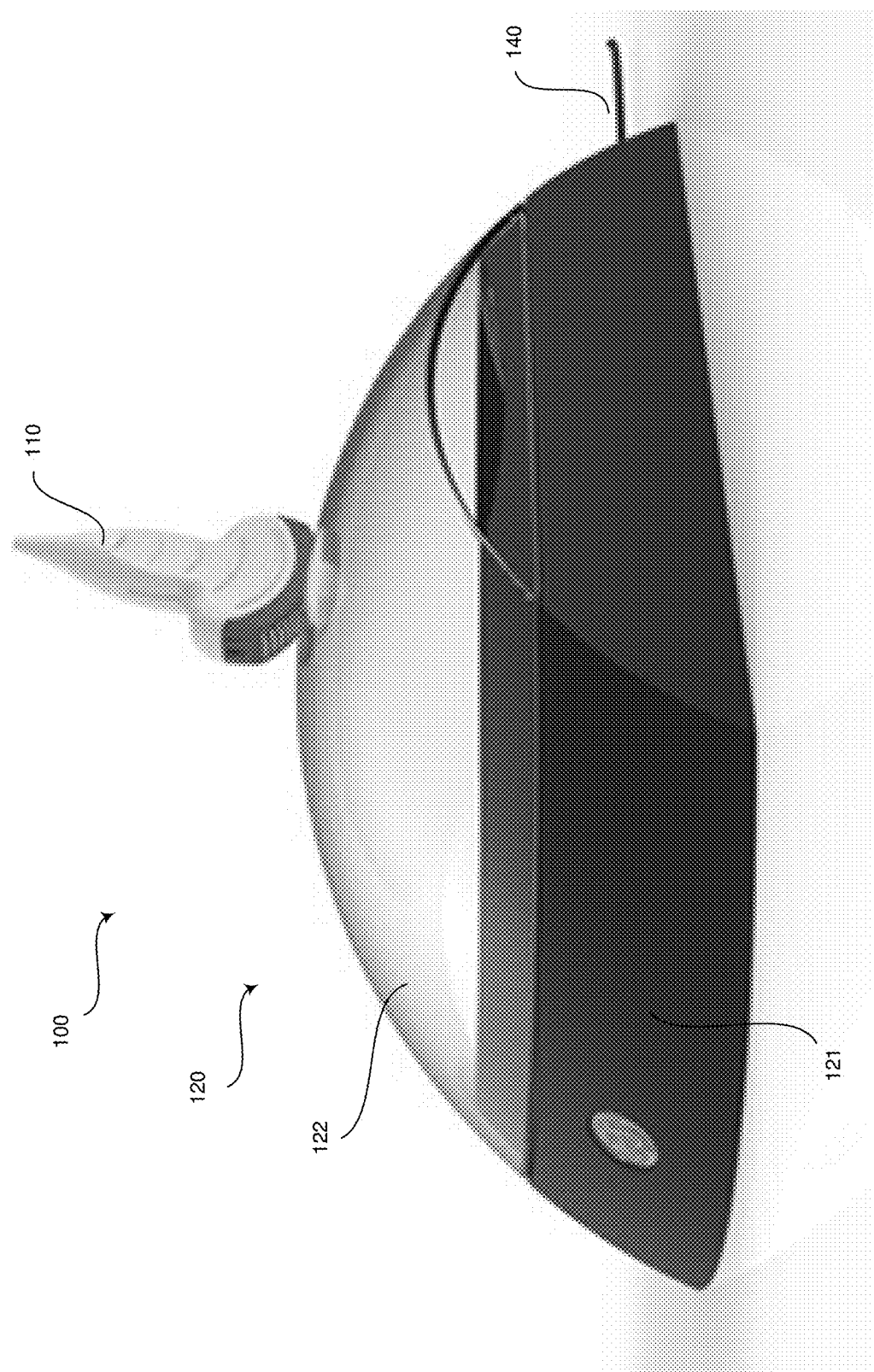
FIG. 9 is a side, perspective view of an exemplary probe simulator and anatomy simulator having a simulated scan surface configured for an external simulated ultrasound examination, in accordance with an embodiment of the disclosure.

FIG. 7 illustrates an exemplary camera 130 of an anatomy simulator 120 acquiring image data 132 of a probe simulator 110 for an external simulated ultrasound examination, in accordance with an embodiment of the disclosure. FIG. 8 is a top, perspective view of an exemplary probe simulator 110 and anatomy simulator 120 having a simulated scan surface 122 configured for an external simulated ultrasound examination, in accordance with an embodiment of the disclosure. FIG. 9 is a side, perspective view of an exemplary probe simulator 110 and anatomy simulator 120 having a simulated scan surface 122 configured for an external simulated ultrasound examination, in accordance with an embodiment of the disclosure. Referring to FIGS. 7-9, the simulation system 10 includes a probe simulator 110 and an anatomy simulator 120 communicatively coupled to a computer system 200 by a communications connection 140. The probe simulator 110 may include a visually coded pattern 113 that can be imaged by a camera 130 of the anatomy simulator 120 during a scanning session when the probe simulator 110 is placed on and/or manipulated about a simulated scan surface 122 of the anatomy simulator 120.

The anatomy simulator 120 may include the simulated scan surface 122 attached to and/or integrated with a base 121 having the camera 130 disposed therein. The camera 130 may be arranged in a fixed position within or on the base 121 so that it has a field of view 136 extending to cover at least a portion of the simulated scan surface 122. The camera may continuously acquire images 132 at a rate of 30 frames/second or any suitable rate if the simulation session is in an unfreeze mode. The acquired images 132 may include image data of a visually coded pattern 113 on the probe simulator 110 if the probe simulator 110 is properly oriented and placed against the simulated scan surface 122. The simulated scan surface 122 may be substantially transparent so that the camera 130 on one side of the simulated scan surface 122 is capable of imaging the visually coded pattern 113 on the probe simulator 110 on an opposite side of the simulated scan surface 122. In an exemplary embodiment, the simulated scan surface 122 may have a shape and/or rigidity that correspond with a patient's anatomy.

In various embodiments, the base 121 of the anatomy simulator may have a top surface 123. The camera may be positioned on the top surface 123 and/or the top surface 123 may include an opening. The camera 130 may acquire images 132 through the opening and/or the camera 130 may extend through the opening in the top surface 123 to acquire the images 132. In certain embodiments, an image 124 of a simulated internal portion of anatomy (e.g., heart or fetus) may be displayed on the top surface 123 and viewable by an operator of the simulation system 10 through the substantially transparent simulated scan surface 122. For example, the top surface 123 may be a display screen (e.g., a light emitting diode or liquid crystal display) that may be configured to display an image 124 of a simulated internal portion of anatomy. Additionally and/or alternatively, the image 124 of the simulated internal portion of anatomy may be projected onto the top surface 123 of the base. For example, a projector may be positioned on the base 121, simulated scan surface 122, or any suitable location for projecting an image onto the top surface 123 of the base 121.

The simulators 100 illustrated in FIGS. 7-9 share various characteristics with the probe simulator 110 and anatomy simulator 120 (collectively referred to as simulators 100) illustrated in FIGS. 1-6 as described above.

Figure 10:
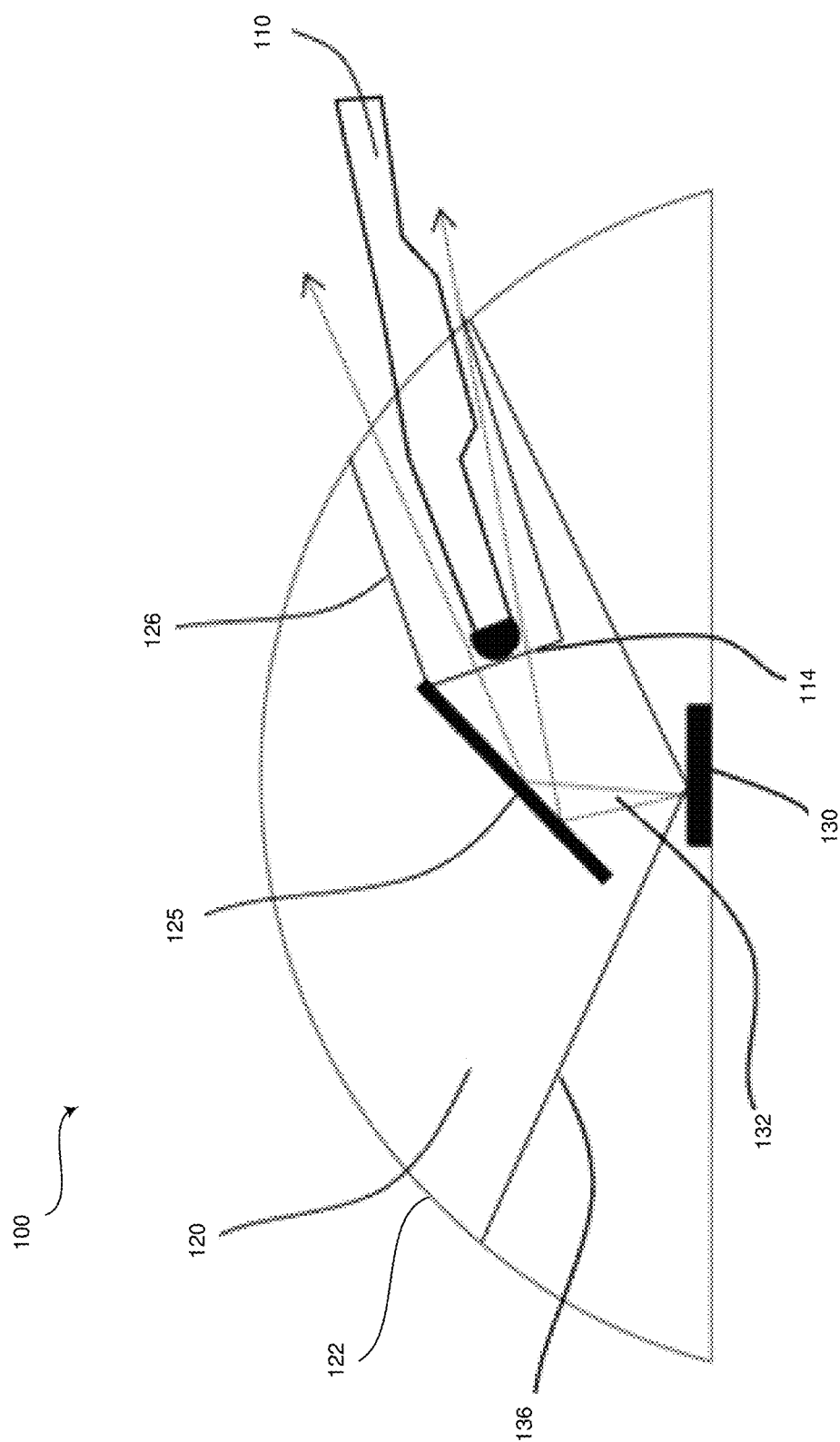
FIG. 10 illustrates an exemplary camera of an anatomy simulator acquiring image data of a probe simulator for an internal simulated ultrasound examination, in accordance with an embodiment of the disclosure.
Figure 11:
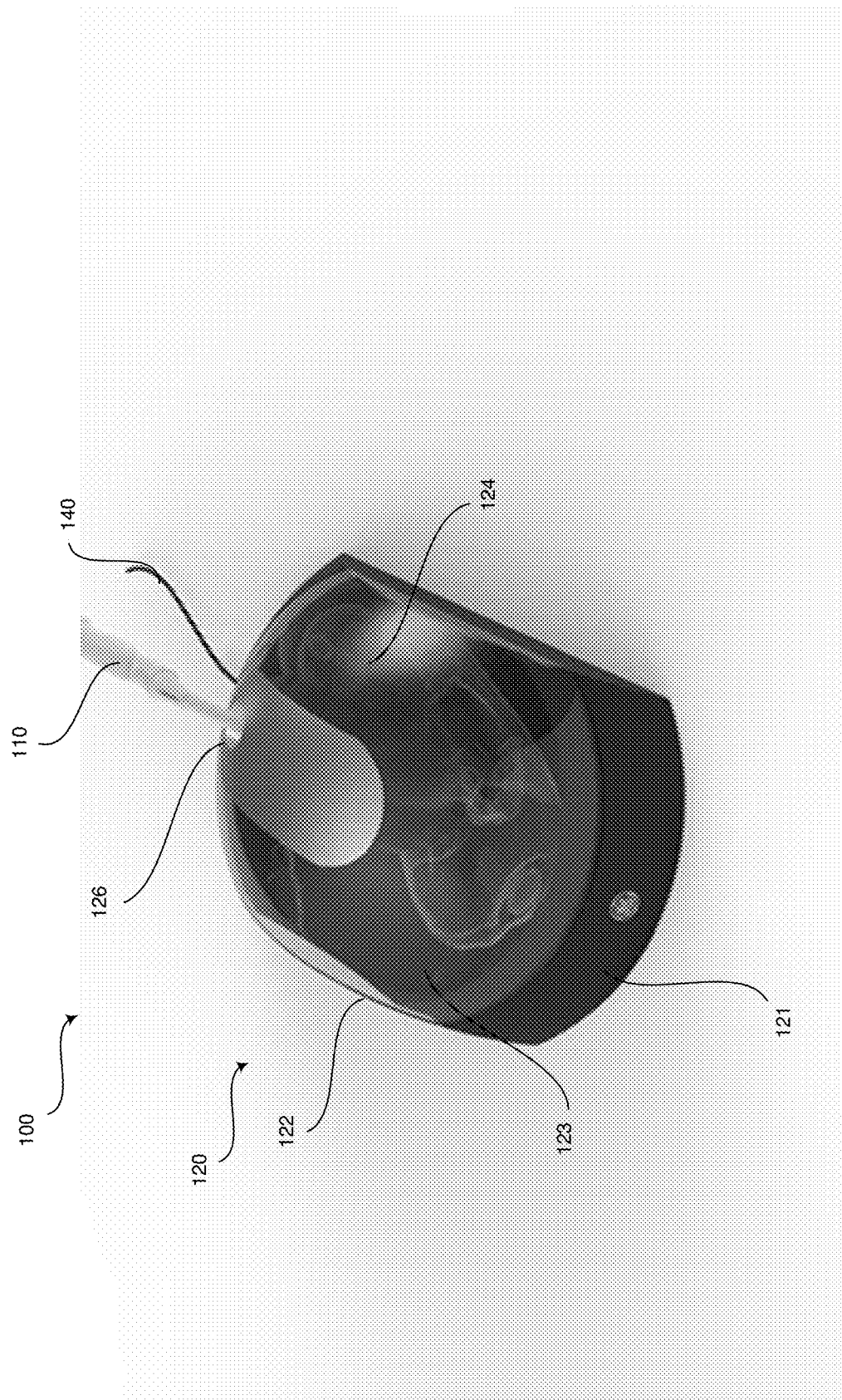
FIG. 11 is a top, perspective view of an exemplary probe simulator and anatomy simulator having a simulated scan surface configured for an internal simulated ultrasound examination, in accordance with an embodiment of the disclosure.
Figure 12:
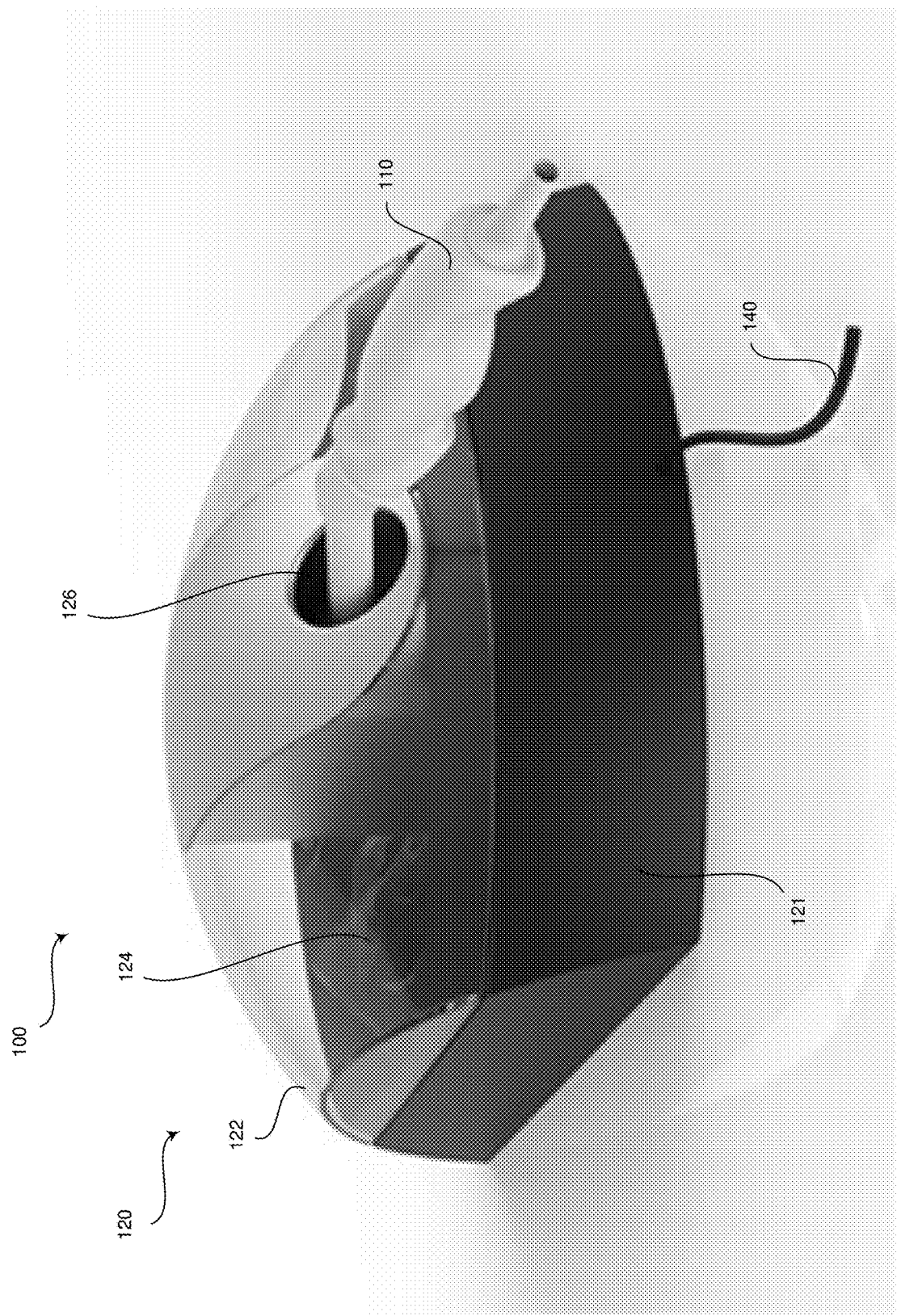
FIG. 12 is a side, perspective view of an exemplary probe simulator and anatomy simulator having a simulated scan surface configured for an internal simulated ultrasound examination, in accordance with an embodiment of the disclosure.

FIG. 10 illustrates an exemplary camera 130 of an anatomy simulator 120 acquiring image data 132 of a probe simulator 110 for an internal simulated ultrasound examination, in accordance with an embodiment of the disclosure. FIG. 11 is a top, perspective view of an exemplary probe simulator 110 and anatomy simulator 120 having a simulated scan surface 122 configured for an internal simulated ultrasound examination, in accordance with an embodiment of the disclosure. FIG. 12 is a side, perspective view of an exemplary probe simulator 110 and anatomy simulator 120 having a simulated scan surface 122 configured for an internal simulated ultrasound examination, in accordance with an embodiment of the disclosure. Referring to FIGS. 10-12, the simulation system 10 includes a probe simulator 110 and an anatomy simulator 120 communicatively coupled to a computer system 200 by a communications connection 140. The probe simulator 110 may include a visually coded pattern 113 that can be imaged by a camera 130 of the anatomy simulator 120 during a scanning session when the probe simulator 110 is placed in and/or manipulated about a cavity 126 of a simulated scan surface 122 of the anatomy simulator 120. The probe simulator 110 may be shaped and/or sized to fit within the cavity 126 of the simulated scan surface 122 of the anatomy simulator 120. For example, the probe simulator 110 may be shaped and/or sized similar to a transvaginal probe, endorectal probe, transesophageal probe, and/or any suitable probe shape and size associated with the cavity 126 of the simulated scan surface 122 of the anatomy simulator 120. In various embodiments, the probe simulator 110 may include an illumination source for providing lighting within the cavity 126 of the simulated scan surface 122 to increase the visibility of the visually coded pattern 113 by a camera 130.

The anatomy simulator 120 may include the simulated scan surface 122 attached to and/or integrated with a base 121 having the camera 130 disposed on or within a top surface 123 of the base 121. The simulated scan surface 122 may include a cavity 126 to simulate an internal ultrasound examination. The end of the cavity 126 may be substantially transparent so that the camera 130 on one side of the cavity 126 is capable of imaging the visually coded pattern 113 on the probe simulator 110 on an opposite side of the cavity 126. In an exemplary embodiment, the cavity 126 may have a shape and/or rigidity that correspond with a patient's anatomy. In various embodiments, the cavity 126 may include an illumination source for providing lighting within the cavity 126 to increase the visibility of the visually coded pattern 113 of the probe simulator 110 by the camera 130. The camera 130 may be arranged in a fixed position within or on the base 121. A mirror or prism 125 may be arranged in a fixed position within the anatomy simulator 120 and within the field of view 136 of the camera 130 to assist the camera 130 in providing image data 132 of the probe simulator maneuvered at a probe placement location 114 within the cavity 126 of the simulated scan surface 122. The camera may continuously acquire images 132 at a rate of 30 frames/second or any suitable rate if the simulation session is in an unfreeze mode. The acquired images 132 may include image data of a visually coded pattern 113 on the probe simulator 110 if the probe simulator 110 is properly oriented and placed against the end of cavity 126 of the simulated scan surface 122. In certain embodiments, an image 124 of a simulated internal portion of anatomy (e.g., heart or fetus) may be displayed on the top surface 123 and viewable by an operator of the simulation system 10 through the substantially transparent simulated scan surface 122.

The simulators 100 illustrated in FIGS. 10-12 share various characteristics with the probe simulator 110 and anatomy simulator 120 (collectively referred to as simulators 100) illustrated in FIGS. 1-9 as described above.

Figure 13:
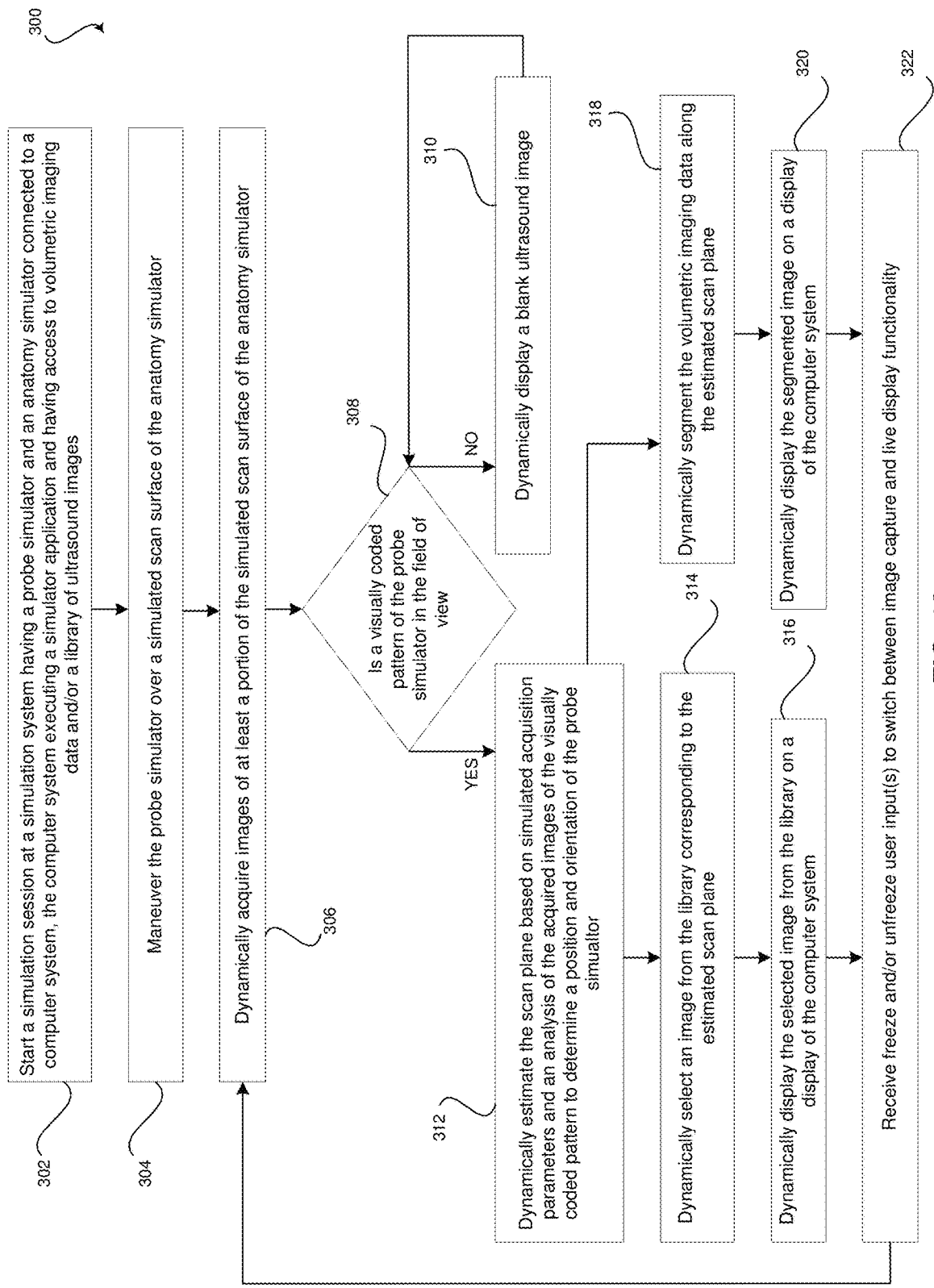
FIG. 13 is a flow chart illustrating exemplary steps that may be utilized for simulating an ultrasound scanning session, in accordance with an embodiment of the disclosure.

FIG. 13 is a flow chart 300 illustrating exemplary steps 302-322 that may be utilized for simulating an ultrasound scanning session, in accordance with an embodiment of the disclosure. Referring to FIG. 13, there is shown a flow chart 300 comprising exemplary steps 302 through 322. Certain embodiments of the present disclosure may omit one or more of the steps, and/or perform the steps in a different order than the order listed, and/or combine certain of the steps discussed below. For example, some steps may not be performed in certain embodiments of the present disclosure. As a further example, certain steps may be performed in a different temporal order, including simultaneously, than listed below.

At step 302, a simulation session is started at a simulation system 10 having a probe simulator 110 and an anatomy simulator 120 communicatively coupled to a computer system 200 executing a simulator application. The computer system 200 may have access to volumetric imaging data and/or a library of ultrasound images. The probe simulator 110 may have a simulated transducer surface 112 including a visually coded pattern 113. The anatomy simulator 120 may include a camera 130 disposed in or on a base 121 and a simulated scan surface 122 coupled to and/or integrated with the base 121. The camera 130 of the anatomy simulator may be configured to transmit acquired image data of at least a portion of the simulated scan surface 122 to the computer system 200 via a wired or wireless communication connection 140. The computer system 200 may include a processor 210, a user input module 230, a display system 230, and memory and/or data storage 220 configured to store the simulation application and pre-acquired ultrasound image data, such as the library of ultrasound images and/or the volumetric imaging data.

At step 304, the probe simulator 110 is maneuvered over a simulated scan surface 122 of the anatomy simulator 120. For example, the probe simulator 110 may be moved across the simulated scan surface 122 for a simulated external ultrasound examination and/or in a cavity 126 of the simulated scan surface 122 for a simulated internal ultrasound examination. In various embodiments, the simulated scan surface 122 and/or cavity 126 may have a shape and/or rigidity that mimic a patient's anatomy.

At step 306, the camera 130 of the anatomy simulator 120 dynamically acquires images 132 of at least a portion of the simulated scan surface 122. For example, the camera may acquire images 132 within a field of view 136 that includes at least a portion of the simulated scan surface 122. In various embodiments, the anatomy simulator 120 may include a mirror or prism 125 to provide images 132 focused on a cavity 126 of the simulated scan surface 122 for a simulated internal ultrasound examination. The images 132 acquired by the camera 130 of the anatomy simulator 120 may be transmitted via wired or wireless communication 140 to the processor 210 of the computer system 200 for analysis.

At step 308, the processor 210 of the computer system 200 analyzes the acquired images 132 to determine whether the visually coded pattern 113 of the probe simulator 110 is visible in the image data. If the visually coded pattern 113 is not visible in the images 132, a blank ultrasound image is presented at the display system 240 of the computer system 200 at step 310 and the method returns to step 308 for the processor 210 to continue analyzing the acquired images 132 for the visually coded pattern 113. After the processor 210 of the computer system 200 detects the visually coded pattern 113 in the acquired images 132, the method proceeds to step 312.

At step 312, the processor 210 of the computer system 200 dynamically estimates a scan plane 131 based on simulated acquisition parameters and an analysis of the acquired images 132 of the visually coded pattern 113 to determine a position and orientation of the probe simulator 110. The simulated acquisition parameters may be default or user selected parameters, such as depth or any suitable parameter. The visually coded pattern 113 may be designed so that the processor 210 is able to identify portions of the pattern 113 that can be distinguished from other portions of the pattern 113. The processor 210 may analyze the visually coded pattern 113 to determine the position and orientation of the probe simulator 110 based on the identified portion of the distinguishable pattern and known position and orientation information corresponding with the identified portion of the visually coded pattern 113. For example, the processor 210 may determine a position of the probe simulator 110 based on the location of the visually coded pattern 113 in the image 132 with reference to a known anatomy simulator coordinate system 134. The processor 210 may determine an orientation of the probe simulator 110 based on a known relationship between the probe coordinate system 115 and portions of the visually coded pattern 113. The known anatomy simulator coordinate system 134 and the known relationships between the probe coordinate system 115 and portions of the visually coded pattern 113 may be saved in processor memory 210 and/or storage 220 for access by the processor 210 during the analysis of the acquired images 132. The processor 210 may estimate the scan plane 131 based on the determined position and orientation of the probe simulator 110 in combination with default or user selected simulated acquisition parameters such as the depth.

At step 314, if the ultrasound data stored in storage 220 of the computer system 200 is a library of ultrasound images, the processor 210 of the computer system 200 dynamically selects an image 242 from the library corresponding with the estimated scan plane 131. For example, the processor 210 may select an image 242 from the library of ultrasound images that is closest to the scan plane estimated at step 312.

At step 316, the processor 210 dynamically presents the selected image 242 from the library at the display system 240 of the computer system 200. In various embodiments, the processor 210 may process the selected image 242 based on simulated acquisition parameters prior to presentation at the display system 240. For example, the selected image 242 may be processed based on a default or user selected gain parameter or any suitable parameter.

At step 318, if the ultrasound data stored in storage 220 of the computer system 200 is volumetric imaging data, the processor 210 of the computer system 200 dynamically segments the volumetric imaging data along the estimated scan plane 131 to generate an image 242 corresponding with the estimated scan plane 131. For example, the processor 210 may segment the volumetric imaging data to extract the scan plane estimated at step 312 from the volumetric imaging data.

At step 320, the processor 210 dynamically presents the segmented image 242 at the display system 240 of the computer system 200. In various embodiments, the processor 210 may process the segmented image 242 based on simulated acquisition parameters prior to presentation at the display system 240. For example, the segmented image 242 may be processed based on a default or user selected gain parameter or any suitable parameter.

At step 322, if the simulation session is in an unfreeze mode, the method returns to step 306 to continue providing a live display at the display system 240 of the computer system 200 by continuing to dynamically acquire images 132 of at least a portion of the simulated scan surface 122 of the anatomy simulator 120. If the processor 210 receives a freeze command via the user input module 230 of the computer system 200, the simulation session switches to a freeze mode so that the currently displayed image 242 may be captured and/or viewed by an operator of the simulation system 10. The image 242 may be saved to storage 220 and/or presented as a still image at the display system 240 of the computer system 200. The method returns to step 306 if the processor 210 receives an unfreeze command via the user input module 230 of the computer system. The operator may provide freeze and/or unfreeze user input(s) via the user input module 230 to the processor 210 of the computer system 200 to switch between image capture and live display functionality.

Aspects of the present disclosure provide a system 10 and method 300 for simulating an ultrasound scanning session. In accordance with various embodiments, a method 300 may comprise acquiring 306, by a camera 130, an image 132 of at least a portion of a simulated scan surface 122. A probe simulator 110 having a visually coded pattern 113 is maneuvered 304 on the simulated scan surface 122. The method 300 may comprise analyzing 312, by a processor 210, the acquired image 132 to identify the visually coded pattern 113 of the probe simulator 110 maneuvered on the simulated scan surface 122. The method 300 may comprise determining 312, by the processor 210, a position and orientation of the probe simulator 110 based on the visually coded pattern 113 identified in the acquired image 132. The method 300 may comprise estimating 312, by the processor 210, a scan plane 131 based at least in part on the determined position and orientation of the probe simulator 110. The method 300 may comprise retrieving 314, 318, by the processor 210, an ultrasound image 242 from storage 220. The ultrasound image 242 may correspond with the estimated scan plane 131. The method 300 may comprise presenting 316, 320, via a display system 240, the retrieved ultrasound image 242.

In various embodiments, the probe simulator 110 is maneuvered in a cavity 126 on the simulated scan surface 122. In certain embodiments, the scan plane 131 is estimated by the processor 210 based on the determined position and orientation of the probe simulator 110 and at least one simulated acquisition parameter. The at least one simulated acquisition parameter may comprise a depth parameter. The depth parameter may be one of a default parameter or a user-defined parameter provided via a user input module 230. In a representative embodiment, the ultrasound image 242 is retrieved by segmenting the ultrasound image 242 from volumetric imaging data along the estimated scan plane 131. In various embodiments, the ultrasound image 242 is retrieved by selecting the ultrasound image 242 from a library of ultrasound images based on the estimated scan plane 131. Each of the ultrasound images in the library of ultrasound images may be associated with at least one scan plane.

In a representative embodiment, the method 300 may comprise presenting 310, via the display system 240, a blank image if the processor 210 does not identify the visually coded pattern 113 of the probe simulator 110 in the acquired image 132. In certain embodiments, the method 300 may comprise presenting a simulated anatomical image 124 on a top surface 123 of a base 121 one or both of attached to or integrated with the simulated scan surface 122. In various embodiments, the method 300 comprises dynamically repeating 322 the steps to provide a live display at the display system 240 if operating in an unfreeze mode. The method 300 may comprise continuing 322 to present the retrieved ultrasound image 242 at the display system 240 if operating in a freeze mode. The method 300 may comprise receiving 322 a user input at the processor 210, via a user input module 230, to switch between the unfreeze mode and the freeze mode. In a representative embodiment, the method 300 may comprise processing 316, 320, by the processor 210, the retrieved ultrasound image 242 based on at least one simulated acquisition parameter. The at least one simulated acquisition parameter may comprise a gain parameter. The gain parameter may be one of a default parameter or a user-defined parameter provided via a user input module 230.

In accordance with various embodiments, a system 10 may comprise a probe simulator 110, a simulated scan surface 122, a camera 130, a processor 210, and a display system 240. The probe simulator 110 may include a simulated transducer surface 112 comprising a visually coded pattern 113. The probe simulator 110 may be configured to maneuver on the simulated scan surface 122. The camera 130 may be configured to acquire an image 132 of at least a portion of the simulated scan surface 122. The processor 210 may be configured to analyze the acquired image 132 to identify the visually coded pattern 113 of the probe simulator 110 maneuvered on the simulated scan surface 122. The processor 210 may be configured to determine a position and orientation of the probe simulator 110 based on the visually coded pattern 113 identified in the acquired image 132. The processor 210 may be configured to estimate a scan plane 131 based at least in part on the determined position and orientation of the probe simulator 110. The processor 210 may be configured to retrieve an ultrasound image 242 from storage 220. The ultrasound image 242 may correspond with the estimated scan plane 131. The display system 240 may be configured to present the retrieved ultrasound image 242.

In certain embodiments, the system 10 may comprise a mirror 125 positioned with respect to the camera 130 so that the image 132 acquired by the camera 130 comprises image data of a cavity 126 of the simulated scan surface 122. In various embodiments, the simulated scan surface 122 may comprise one or both of a shape and a rigidity simulating a patient anatomy. In a representative embodiment, the processor 210 is configured to retrieve the ultrasound image 242 by segmenting the ultrasound image 242 from volumetric imaging data along the estimated scan plane 131. In certain embodiments, the processor 210 is configured to retrieve the ultrasound image 242 by selecting the ultrasound image 242 from a library of ultrasound images based on the estimated scan plane 131. Each of the ultrasound images in the library of ultrasound images may be associated with at least one scan plane.

In various embodiments, the processor 210 is configured to estimate the scan plane 131 based on the determined position and orientation of the probe simulator 110 and at least one simulated acquisition parameter. The at least one simulated acquisition parameter may comprise a depth parameter. The depth parameter may be one of a default parameter or a user-defined parameter provided via a user input module 230. In certain embodiments, the processor 210 is configured to process the retrieved ultrasound image 242 based on at least one simulated acquisition parameter. The at least one simulated acquisition parameter may comprise a gain parameter. The gain parameter may be one of a default parameter or a user-defined parameter provided via a user input module 230. In a representative embodiment, the simulated scan surface 122 may be integrated with and/or attached to a base 121 having a top surface 123. A simulated anatomical image 124 may be presented on the top surface 123.

Certain embodiments provide a non-transitory computer readable medium having stored computer program comprises at least one code section that is executable by a machine for causing the machine to perform steps 300 disclosed herein. Exemplary steps 300 may comprise acquiring 306 an image 132 of at least a portion of a simulated scan surface 122. A probe simulator 110 having a visually coded pattern 113 may be maneuvered 304 on the simulated scan surface 122. The steps 300 may comprise analyzing 312 the acquired image 132 to identify the visually coded pattern 113 of the probe simulator 110 maneuvered on the simulated scan surface 122. The steps 300 may comprise determining 312 a position and orientation of the probe simulator 110 based on the visually coded pattern 113 identified in the acquired image 132. The steps 300 may comprise estimating 312 a scan plane 131 based at least in part on the determined position and orientation of the probe simulator 110. The steps 300 may comprise retrieving 314, 318 an ultrasound image 242 from storage 220. The ultrasound image 242 may correspond with the estimated scan plane 131. The steps 300 may comprise presenting 316, 320 the retrieved ultrasound image 242 at a display system 240.

In a representative embodiment, the scan plane 131 may be estimated based on the determined position and orientation of the probe simulator 110 and at least one simulated acquisition parameter. The at least one simulated acquisition parameter may comprise a depth parameter. The depth parameter may be a default parameter or a user-defined parameter. In various embodiments, the ultrasound image 242 may be retrieved by segmenting 318 the ultrasound image 242 from volumetric imaging data along the estimated scan plane 131. In certain embodiments, the ultrasound image 242 may be retrieved by selecting 314 the ultrasound image 242 from a library of ultrasound images based on the estimated scan plane 131. Each of the ultrasound images in the library of ultrasound images may be associated with at least one scan plane. In a representative embodiment, the steps 300 may comprise dynamically repeating 322 the steps 306-322 to provide a live display at the display system 240 if operating in an unfreeze mode. The steps 300 may comprise continuing 322 to present the retrieved ultrasound image 242 at the display system 240 if operating in a freeze mode. The steps 300 may comprise receiving 322 a user input to switch between the unfreeze mode and the freeze mode.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set {(x), (y), (x, y)}. As another example, "x, y, and/or z" means any element of the seven-element set {(x), (y), (z), (x, y), (x, z), (y, z), (x, y, z)}. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "configured" and/or "operable" to perform a function whenever the circuitry comprises the necessary hardware and code (if any is necessary) to perform the function, regardless of whether performance of the function is disabled, or not enabled, by some user-configurable setting.

Other embodiments may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for simulating an ultrasound scanning session.

Accordingly, certain embodiments may be realized in hardware, software, or a combination of hardware and software. Various embodiments may be realized in a centralized fashion in at least one computer system, or in a distributed fashion where different elements are spread across several interconnected computer systems. Any kind of computer system or other apparatus adapted for carrying out the methods described herein is suited. A typical combination of hardware and software may be a general-purpose computer system with a computer program that, when being loaded and executed, controls the computer system such that it carries out the methods described herein.

Various embodiments may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What is claimed is:

1. A method, comprising:
   acquiring, by a camera, an image of at least a portion of a simulated scan surface, wherein a probe simulator comprising a simulated transducer surface having a visually coded pattern is maneuvered on a first side of the simulated scan surface, and wherein the camera is positioned on a second side of the simulated scan surface opposite the first side;
   analyzing, by a processor, the acquired image to identify the visually coded pattern of the simulated transducer surface of the probe simulator maneuvered on the first side of the simulated scan surface;
   determining, by the processor, a position and orientation of the probe simulator based on the visually coded pattern identified in the acquired image;
   estimating, by the processor, a scan plane based at least in part on the determined position and orientation of the probe simulator;
   retrieving, by the processor, an ultrasound image from storage, wherein the ultrasound image corresponds with the estimated scan plane; and
   presenting, via a display system, the retrieved ultrasound image.

2. The method according to claim 1, wherein the probe simulator is maneuvered in a cavity on the simulated scan surface.

3. The method according to claim 1, wherein:
   the scan plane is estimated by the processor based on the determined position and orientation of the probe simulator and at least one simulated acquisition parameter,
   the at least one simulated acquisition parameter comprises a depth parameter, and
   the depth parameter is one of a default parameter or a user-defined parameter provided via a user input module.

4. The method according to claim 1, wherein the ultrasound image is retrieved by segmenting the ultrasound image from volumetric imaging data along the estimated scan plane.

5. The method according to claim 1, wherein the ultrasound image is retrieved by selecting the ultrasound image from a library of ultrasound images based on the estimated scan plane, and wherein each of the ultrasound images in the library of ultrasound images is associated with at least one scan plane.

6. The method according to claim 1, comprising presenting, via the display system, a blank image if the processor does not identify the visually coded pattern of the probe simulator in the acquired image.

7. The method according to claim 1, comprising presenting a simulated anatomical image on a top surface of a base one or both of attached to or integrated with the simulated scan surface.

8. The method according to claim 1, comprising:
   dynamically repeating the steps of claim 1 to provide a live display at the display system if operating in an unfreeze mode,
   continuing to present the retrieved ultrasound image at the display system if operating in a freeze mode, and
   receiving a user input at the processor, via a user input module, to switch between the unfreeze mode and the freeze mode.

9. The method according to claim 1, comprising processing, by the processor, the retrieved ultrasound image based on at least one simulated acquisition parameter, wherein the at least one simulated acquisition parameter comprises a gain parameter, and wherein the gain parameter is one of a default parameter or a user-defined parameter provided via a user input module.

10. A system, comprising:
a probe simulator having a simulated transducer surface comprising a visually coded pattern;
a simulated scan surface, wherein the probe simulator is configured to maneuver on a first side of the simulated scan surface;
a camera positioned on a second side of the simulated scan surface opposite the first side, the camera configured to acquire an image of at least a portion of the simulated scan surface;
a processor configured to:
analyze the acquired image to identify the visually coded pattern of the simulated transducer surface of the probe simulator maneuvered on the first side of the simulated scan surface,
determine a position and orientation of the probe simulator based on the visually coded pattern identified in the acquired image,
estimate a scan plane based at least in part on the determined position and orientation of the probe simulator, and
retrieve an ultrasound image from storage, wherein the ultrasound image corresponds with the estimated scan plane; and
a display system configured to present the retrieved ultrasound image.

11. The system according to claim 10, comprising a mirror positioned with respect to the camera so that the image acquired by the camera comprises image data of a cavity of the simulated scan surface.

12. The system according to claim 10, wherein the simulated scan surface comprises one or both of a shape and a rigidity simulating a patient anatomy.

13. The system according to claim 10, wherein the processor is configured to retrieve the ultrasound image by one of:
segmenting the ultrasound image from volumetric imaging data along the estimated scan plane, or
selecting the ultrasound image from a library of ultrasound images based on the estimated scan plane, each of the ultrasound images in the library of ultrasound images being associated with at least one scan plane.

14. The system according to claim 10, wherein the processor is configured to one or both of:
estimate the scan plane based on the determined position and orientation of the probe simulator and at least one simulated acquisition parameter, the at least one simulated acquisition parameter comprising a depth parameter, and the depth parameter being one of a default parameter or a user-defined parameter provided via a user input module, and
process the retrieved ultrasound image based on at least one simulated acquisition parameter, the at least one simulated acquisition parameter comprising a gain parameter, and the gain parameter being one of a default parameter or a user-defined parameter provided via a user input module.

15. The system according to claim 10, wherein the simulated scan surface is one of integrated with or attached to a base having a top surface, and wherein a simulated anatomical image is presented on the top surface.

16. A non-transitory computer readable medium having stored thereon, a computer program having at least one code section, the at least one code section being executable by a machine for causing the machine to perform steps comprising:
acquiring an image of at least a portion of a simulated scan surface, wherein a probe simulator comprising a simulated transducer surface having a visually coded pattern is maneuvered on a first side of the simulated scan surface, and wherein the image is acquired from a second side of the simulated scan surface opposite the first side;
analyzing the acquired image to identify the visually coded pattern of the simulated transducer surface of the probe simulator maneuvered on the first side of the simulated scan surface;
determining a position and orientation of the probe simulator based on the visually coded pattern identified in the acquired image;
estimating a scan plane based at least in part on the determined position and orientation of the probe simulator;
retrieving an ultrasound image from storage, wherein the ultrasound image corresponds with the estimated scan plane; and
presenting the retrieved ultrasound image at a display system.

17. The non-transitory computer readable medium according to claim 16, wherein:
the scan plane is estimated based on the determined position and orientation of the probe simulator and at least one simulated acquisition parameter,
the at least one simulated acquisition parameter comprises a depth parameter, and
the depth parameter is one of a default parameter or a user-defined parameter.

18. The non-transitory computer readable medium according to claim 16, wherein the ultrasound image is retrieved by segmenting the ultrasound image from volumetric imaging data along the estimated scan plane.

19. The non-transitory computer readable medium according to claim 16, wherein the ultrasound image is retrieved by selecting the ultrasound image from a library of ultrasound images based on the estimated scan plane, and wherein each of the ultrasound images in the library of ultrasound images is associated with at least one scan plane.

20. The non-transitory computer readable medium according to claim 16, comprising:
dynamically repeating the steps of claim 16 to provide a live display at the display system if operating in an unfreeze mode,
continuing to present the retrieved ultrasound image at the display system if operating in a freeze mode, and
receiving a user input to switch between the unfreeze mode and the freeze mode.

* * * * *